United States Patent [19]

Vincent et al.

[11] 4,404,215

[45] Sep. 13, 1983

[54] PIPERIDYL PHENYL TRIFLUOROETHANOLS

[75] Inventors: Michel Vincent, Bagneux; Georges Remond, Versailles; Jacques Bure, Neuilly-sur-Seine, all of France

[73] Assignee: Science Union et Cie, Suresnes, France

[21] Appl. No.: 322,513

[22] Filed: Nov. 18, 1981

Related U.S. Application Data

[62] Division of Ser. No. 90,635, Nov. 2, 1979, abandoned.

[30] Foreign Application Priority Data

Nov. 3, 1978 [FR] France .................. 78 31096

[51] Int. Cl.³ .......................................... A61K 31/445
[52] U.S. Cl. ................... 424/267; 544/395; 546/262; 564/184; 564/223; 564/443; 424/250; 424/266; 424/320; 424/324; 424/330
[58] Field of Search ........................ 546/223; 424/267

[56] References Cited

U.S. PATENT DOCUMENTS

| | | | |
|---|---|---|---|
| 3,142,683 | 7/1964 | Dice et al. | 546/346 |
| 3,531,487 | 9/1970 | Berger et al. | 546/223 |
| 3,821,231 | 6/1974 | Stanislavovich et al. | 546/223 |
| 4,259,337 | 3/1981 | Nedelec et al. | 546/346 |
| 4,288,453 | 9/1981 | Vincent et al. | 562/426 |
| 4,339,455 | 7/1982 | Sauter et al. | 546/346 |

FOREIGN PATENT DOCUMENTS

1411783 10/1975 United Kingdom ................ 546/223

*Primary Examiner*—Ethel G. Love
*Attorney, Agent, or Firm*—Gordon W. Hueschen

[57] ABSTRACT

This invention relates to novel arylethanol and to process for producing the said compounds.

The arylethanols of the invention have valuable pharmacological properties and find a use in human or animal therapy.

10 Claims, No Drawings

PIPERIDYL PHENYL TRIFLUOROETHANOLS

This is a divisional of application Ser. No. 090,635, filed Nov. 2, 1979, now abandoned.

PRIOR ART

The prior art may be illustrated with the disclosure of U.S. Pat. application Ser. No. 949,571, now U.S. Pat. No. 4,288,453.

SUMMARY OF THE INVENTION

The invention provides ααα-trifluoroaminoarylethanols, i.e., arylethanols, the aryl ring of which is substituted with a free amino or a mono- or disubstituted amino radical.

This invention also relates to a process in which a 4-fluoroarylketone is reacted with an amino derivative to produce the corresponding 4-aminoarylketone which is further reduced or sulfurated into the corresponding ethanol or ethanethiol.

These compounds are endowed with analgetic, anti-inflammatory and anti-pyretic properties. They are of value in pharmaceutical compositions as a drug for treating pain, hyperpyretic conditions and inflammatory states.

PREFERRED EMBODIMENTS

This invention relates to novel arylethanols and to a process for producing the said compounds.

More precisely the invention provides as new compounds, arylethanol derivatives, the aryl radical of which is substituted with a free or substituted amino group.

Specifically this invention provides ααα-trifluoro (aminoaryl) ethanols having the formula I:

$$\begin{array}{c} Z \\ \phantom{Z}\backslash \\ \phantom{ZZ}N-Ar-CH-CF_3 \\ \phantom{ZZ}/ \phantom{XXXXX} | \\ Z' \phantom{XXXXX} Z''R \end{array} \quad (I)$$

wherein

Z is a hydrogen, an alkyl radical having from 1 to 16 carbon atoms, a lower cycloalkyl radical, a N-lower alkyl piperidino radical, a N-aryl lower alkyl piperidino radical, an acyl residue of a carboxylic acid selected from the group consisting of a lower alkyl carboxylic acid, an aryl carboxylic acid of the formula VIII:

$$\begin{array}{c} COOH \\ | \\ \phantom{X}\bigcirc\!-\!(E)_n \end{array} \quad (VIII)$$

in which

E is a lower alkyl radical, a lower alkoxy radical, a cyano radical, a trifluoromethyl, a trifluoromethoxy, a trifluoromethylthio, a lower alkylsulphonyl and a halogen atom
and
n is zero or an integer of 1 to 3
and
a heteroaryl carboxylic acid having the formula IX:

$$\begin{array}{c} COOH \\ A\!-\!\diagup \\ \phantom{X}\big\langle \\ \phantom{X}B \end{array} \quad (IX)$$

wherein

A is —CH=, S, O or NH and B is S, O, NH or —C=N—

Z' is a hydrogen or a lower alkyl radical

Z" is an oxygen or a sulphur atom

Ar is a mono- or bicyclic homocyclic aromatic ring, each ring having from 5 to 7 carbon atoms and R is a hydrogen, a lower alkyl or a lower acyl residue.

The invention also provides the optically-active forms of a compound of formula I. The structure of these compounds incorporates at least one asymetric carbon and this allows, after resolution, to recover the dextrorotatory and the laevorotatory isomers.

The invention also relates to the acid addition salts of a compound of formula I in the racemic form or in any of the optically-active forms. The acid used for the salification step is preferably a non-toxic therapeutically-compatible organic or mineral acid. However other acids may also be used as a separating mean or a purification mean.

As salt-forming acids may be mentioned hydrochloric acid, hydrobromic acid, sulphuric acid, phosphoric acid, perchloric acid, hexametaphosphoric acid, silicic acid; formic acid, acetic acid, butyric acid, dipropylacetic acid, benzoic acid, 2,4-dichlorobenzoic acid, nicotinic acid, thiazolcarboxylic acid, 2-methylthiazolidinyl 4-carboxylic acid, isethionic acid, benzenesulphonic acid, naphthylsulphonic acid, glucose 1-phosphoric acid, glucose 1,6-diphosphoric acid and the like.

The compounds of formula I and their addition salts are endowed with interesting pharmacological properties; namely they exert anti-inflamatory, analgetic and/or antipyretic properties.

These anti-inflammatory properties are evidenced with the Caraghenin test in the rat. The analgetic properties are evidenced with the phenylbenzoquinone, silver nitrate, and acetic acid writhing tests in the mice.

The anti-pyretic properties have been evidenced according to the technique disclosed by J. J. LOUX in Toxicology and Applied Pharmacol. 22 (1972) 672.

Moreover, the compounds of formula I have a very weak toxicity and the first manifestations of intoxication appear in the mice only at very high doses, usually higher than 1,5 g/kg. The nephrotoxicity and the hepatotoxicity of these compounds are very weak, if any, in contrast to the well-known toxicity of paracetamol which appears to be a compound of similar therapeutic use.

The compounds of formula I and the acid addition salts thereof have valuable therapeutic properties and find a therapeutic use in human or veterinary medicine for treating or alleviating painful conditions from medical or surgical origin, such as arthritis, articular diseases, arthrosis, and traumatic conditions. As an anti-inflammatory agent they are of use as medicine for the otolaryngoligic space such as sinusitis and the rheumatoid diseases.

As an antipyretic agent they have a further use for treating the hyperpyretic conditions resulting from an immunological reaction, a viral, a microbial or a parasitic disease, namely, in children, for treating hyperpyretic convulsion.

This invention provides pharmaceutical compositions incorporating as active ingredient at least one compound of formula I in the racemic form or in an optically-active form, or a salt thereof, in conjunction or in admixture with an inert, nontoxic, therapeutically-compatible pharmaceutical carrier or vehicle.

The pharmaceutical compositions according to the invention may further include other active ingredients having a similar or synergistic activity, such as analgetics, steroidal anti-inflammatory drugs, anti-inflammatory drugs having an arylacetic or arylpropionic structure; antispasmodics; sedatives such as barbiturics; anti-bacterials, or antibiotics.

The pharmaceutical compositions are any of those suitable for oral, parenteral, or rectal routes of administration. The percutaneous way, the permucous way and the sublingual way may also be utilized, and the corresponding pharmaceutical formulations are within the scope of this invention.

The useful doses may greatly vary, depending on the age, the weight of the patient, on the severity of the disease to be treated and on the route of administration.

Usually the dosages range from 50 to 600 mg per unit dosage. It may range from 50 to 600 mg for the pharmaceutical compositions intended for oral administration. It may also range from 100 to 500 mg for the pharmaceutical compositions intended for parenteral or rectal administration.

The daily dosage ranges from 0 g 100 to 3 g in man. In animals the daily dosages are calculated on a weight basis. In a preferred manner the oral pharmaceutical compositions incorporate from 150 to 300 mg of active ingredient of formula I. The pharmaceutical compositions designed for parenteral or rectal administration preferably incorporate from 100 to 200 mg of active ingredient of formula I per unit dosage.

Among the pharmaceutical formulations which are within the scope of this invention may more particularly be mentioned tablets, coated tablets, dragees, capsules, soft gelatine capsules, syrups, drinkable suspensions, solutions or suspensions to be injected, packed in ampuls, multi-dosage flasks, vials, auto-injectable syringes, suppositories, sublingual tablets, microgranules, entrapped liposomes, and the like.

The pharmaceutically-acceptable carriers or vehicles are namely starches, chemically-modified celluloses, cellulose, calcium carbonate, calcium phosphate, magnesium phosphate, silica magnesium or titanium silicate, talc, formulated casein; water, sugar syrups, isotonic saline for the liquid formulations, cocoa butter and polyethyleneglycol stearates for the suppositories.

The pharmaceutical compositions according to the invention may also include diluents, fillers, binding agents, emulsifying agents, flavouring agents, colouring matters and/or sweetening agents.

The production of the pharmaceutical compositions is performed according to the methods usually known in the pharmaceutical technology.

As preferred active ingredients the following may be mentioned:

dl 1-(4-acetamidophenyl) 2,2,2-trifluoroethanol
dl 1-(4-propionamidophenyl) 2,2,2 trifluoroethanol
dl 1-(4-isobutyramidophenyl) 2,2,2-trifluoroethanol
dl 4-[(2,2,2-trifluoro 1-hydroxyethyl) aminophenyl] 1-(phenyl 2-ethyl) piperidine.
dl 1-(4-nicotinoylaminophenyl) 2,2,2-trifluoroethanol
dl 1-[(4-chlorobenzoylaminophenyl] 2,2,2-trifluoroethanol
dl 1-(4-acetamidophenyl) 1-ethoxy 2,2,2-trifluoroethane This invention also provides a process for preparing the compounds having the formula I:

wherein the substituents Z, Z', Z", and R have the above-defined meanings,
which comprises the steps of reacting an aminoderivative of formula

wherein Z is a hydrogen, an alkylradical as previously defined, a lower cycloalkyl radical, an N-lower alkyl-piperidino, or an N-aryl lower alkylpiperidino
and Z' is a hydrogen or a lower alkyl radical with a 4-fluoroarylketone having the formula III:

wherein Ar has the above-given definitions to produce a 4-aminoarylketone having the formula IV:

in which Z, Z' and Ar have the above-given definitions and contacting the latter with a reducing agent to produce an arylethanol of the formula V:

in which Z, Z' and Ar are defined as previously given.

The process may also incorporate the further steps of submitting the arylketone of formula IV to the action of a sulphurizing agent to produce the thio-ketone of formula VI:

wherein Z, Z' and Ar keep the above-given definitions and reducing the latter by means of a hydrogenating agent to produce the corresponding thiol of the formula VII:

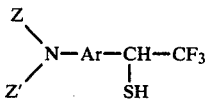

(VII)

in which the substituents Z, Z' and Ar have the above-given definitions.

The arylethanols of formula V and the arylthiols of formula VII may be further alkylated by means of an alkylating agent such as a lower alkyl halide or acylated by means of a functional derivative of a lower alkyl carboxylic acid
  to produce a compound of formula I in which R is a lower alkyl radical or the acyl residue of a lower alkyl carboxylic acid.

When Z and/or Z' is a hydrogen, the compounds of formula I or the compounds of formula IV may be further acylated by means of a lower alkyl- or an arylcarboxylic acid or a functional derivative thereof to produce a compound of formula IV or of formula I wherein Z is an acyl residue derived from a lower alkyl carboxylic acid or from an aryl carboxylic acid which is further reduced to a compound of formula I wherein Z is an acyl residue.

The herein-before defined process further includes the optional step of salifying the compounds of formula I by adding a mineral or organic acid, preferably a therapeutically-compatible acid.

The process according to this invention further includes the optional step of resolving a racemic mixture by means of a chemical or biochemical chiral reagent and separating the resolved isomers.

According to the preferred features of the process, the invention may be further defined as follows:
(1) the step of reaction between the 4-fluoro derivative III and the amino derivative II is performed in an aprotic polar solvent such as dimethylformamide, dimethylacetamide, sulpholane, dimethylsulfoxide, hexamethylphosphoramide, or tetramethylurea,
(2) the step of reaction between the 4-fluoro derivative III and the amino derivative II is performed in the presence of a proton-acceptor,
(3) the reduction of a 4-aminoarylketone of formula IV is performed by means of a mixed alkalimetal hydride such as a lithium aluminohydride, an alkalimetal borohydride, by means of catalytic hydrogenation, or by metathesis with a hydroxylated reagent according to the MEERWEIN PONDORFF's method.
(4) the sulphurizing agent is phosphorous pentasulphide, the complex $P_4S_{10}$-4 pyridine, or an alkalimetal sulphide,
(5) the hydrogenation of the thioketone of formula VI is performed using an alkalimetal borohydride or by means of a catalytic hydrogenation in the presence of palladium, rhodium or rhenium
(6) the alkylation of the compounds of formula V or formula VII is performed using a lower alkyl chloride or bromide in a basic medium,
(7) the acylation of the compounds of formula V or formula VII is performed using a lower alkylcarboxylic acid chloride in the presence of a pyridinic base, preferably pyridine or 4-dimethylaminopyridine,
(8) the acylation of the compounds of formula IV or of formula I wherein Z is a hydrogen, is performed by means of an alkylcarboxylic acid, an acid of formula VIII, or a heteroarylcarboxylic acid of formula IX or a functional derivative thereof such as the mixed anhydride produced in situ by reaction with dicyclohexylcarbodiimide, ethylchloroformate or an acid chloride in the presence of triethylamine.
(9) the resolution of the compounds of formula I is performed either by salifying a compound of formula I by an optically-active organic acid or esterifying a compound of formula I with an optically-active organic acid; the suitable optically-active acids are namely dibenzoyl d-tartaric acid, 1-menthoxyacetic acid, abietic acid, ditoluyltartaric acid, d-camphanic acid, and the like. The resulting salts or the resulting esters are further hydrolysed and the resolved compounds are then recovered.

As far as the invention is concerned, a lower alkyl radical is defined as having from 1 to 5 carbon atoms. Examples of such lower alkyl radicals are methyl, ethyl, n-propyl, isopropyl, secbutyl, tertbutyl, neopentyl, and n-pentyl radicals.

A lower alkoxy radical is defined as a lower alkyloxy radical having from 1 to 6 carbon atoms in the alkyl moiety, in straight or branched chain. Examples of preferred lower alkoxy are methoxy, ethoxy, isopropoxy, n-butoxy, secbutoxy, tertamyloxy, n-hexyloxy.

An aryl lower alkyl radical is a phenyl or substituted phenylalkyl radical, the alkyl moiety of which has from 1 to 4 carbon atoms. When aryl means a substituted phenyl, the phenyl ring bears one or more substituents selected from the group consisting of halogen, lower alkoxy, amino, lower alkyl, lower acylamino, dilower alkylamino, lower alkylamino or a lower alkylenedioxy.

As preferred aryl(lower alkyl) groups may be cited the benzyl, phenethyl, γ-phenylpropyl, β-methylphenethyl, 3,4-dimethoxybenzyl, 2,6-dichlorobenzyl, 2,6-dimethylbenzyl, 3,4,5-trimethoxybenzyl, 3,4-methylenedioxybenzyl, syringyl, p-acetylaminobenzyl, and 3-trifluoromethylbenzyl.

When Z is a lower cycloalkyl radical, it may be a cyclopropyl, a 2,2-dimethylcyclopropyl, a 1-tertbutylcyclopropyl, a cyclobutyl, a cyclopentyl, a cyclohexyl, or a 2,6-dimethylcyclohexyl radical.

When Ar is a monocyclic aromatic ring, it may be defined as a phenyl or substituted phenyl of the general formula:

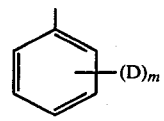

wherein D is a substituent selected from the group consisting of halogen, lower alkyl, lower alkoxy, lower alkenyloxy, lower alkynyloxy, lower alkylthio, carboxy, lower alkylcarbonyl, nitro, aminosulphonyl, lower alkylaminosulphonyl, dilower alkylaminosulphonyl, lower alkylsulphonyl, cyano, trifluoromethyl, and lower alkylenedioxy m is an integer of 1 to 4

The following examples are merely intended to illustrate the invention. They do not limit it in any manner.

EXAMPLE 1

1-(4-acetamidophenyl) 2,2,2-trifluoroethanol

Step A 1-(4-acetamidophenyl) 2,2,2-trifluoroethanol

In a sealed vessel 50 g 4-fluoro ααα-trifluoroacetophenone are introduced together with 500 ml of an ethanolic solution of ammonia saturated at room temperature. The whole mixture is heated to 140° under stirring for about 30 hours.

After return to room temperature, the whole mixture is taken out, the gas removed and evaporated to dryness. The dry residue is taken up with 150 ml ether and the insoluble matters are separated by filtration. The ethereous phase is then washed 3 or 4 times with 2 N hydrochloric acid. The aqueous phases are separated and united, then neutralized by adding an aqueous saturated solution of sodium bicarbonate. The precipitate is separated by suction-filtration, washed with water and dried under reduced pressure. The residue weighing 15.4 g substantially consists of 4-amino ααα-trifluoroacetophone.

From the ethereous mother liquors, a second crop is obtained providing a semi-crystallized product weighing 1.8 g.

A further crop may be also be obtained by retreating the residue from the evaporation of the mother liquors, weighing 4.7 g. The total yield amounts to about 52%. The starting material is obtained according to the process disclosed in the French patent of addition N°78.12452 on Apr. 27, 1978.

Step B 4-acetamido ααα-trifluoroacetophenone

In a three-neck flask, 10 g 4-amino ααα-trifluoroacetophenone from step A, 5.86 g triethylamine and 60 ml benzene are added. To the clear solution 4.5 g acetylchloride are added slowly under stirring and keeping the internal temperature below 10° by means of iced water bath. This addition takes about 20 mn. Then after completion the reaction mixture is kept under stirring for 3 hours at room temperature. The excess of reagent is destroyed by adding a few drops of 40% sodium hydroxide and then 10 ml water. The benzenic phase is separated, washed with water and then with a saturated aqueous solution of sodium bicarbonte and finally with water until the washings are neutral. The benzenic solution is dried on sodium sulphate, filtered and evaporated off under reduced pressure.

8.7 g 4-acetamido ααα-trifluoroacetophenone are thus recovered. For analytical purpose a sample is recrystallized from isopropyl ether.

The pure compound melts at 82°. It is used totally for the next step of the synthesis.

Step C 8.2 g 1-(4-acetamidophenyl) 2,2,2-trifluoroethanol 8.2 g 4-acetamido ααα-trifluoroacetophenone from step B are dissolved in 120 ml methanol and to this solution, 2.85 g sodium borohydride are added portionwise while maintaining the temperature of the reaction medium below 10° by means of a waterbath. After completion of the addition the mixture is kept under stirring at 10° C. for a further hour. The excess of reagent is des-destroyed with few ml of 50% acetic acid. The mixture is diluted with an equal volume of water. The aqueous solution is extracted 3 times with 25 ml ether. The ethereous solutions are united, washed with water until the washings are neutral, then dried on sodium sulphate and evaporated to dryness.

The dry residue weighing 9.46 g is recovered and further purified by recrystallizing it from cyclohexane. 6.84 g of 1-(4-acetamidophenyl) 2,2,2-trifluoroethanol are then obtained as white crystals, insoluble in water and soluble in methanol and ethanol. The pure compound melts at 157°–158°.

ANALYSIS: $C_{10}H_{10}F_3NO_2 = 233.20$.

|  | C | H | N % |
| --- | --- | --- | --- |
| Calculated | 51.51 | 4.32 | 6.00 |
| Found | 51.33 | 4.50 | 6.18 |

EXAMPLE 2

1-(4-isobutyramidophenyl) 2,2,2-trifluoroethanol

Using the same procedure as in example 1 the following compounds have been obtained:

4-isobutyramido ααα-trifluoroacetophenone used as such for the next step, 1-(4-isobutyramidophenyl) 2,2,2-trifluoroethanol as colourless crystals, insoluble in water and soluble in most of the organic solvents. It melts at 150°.

ANALYSIS: $C_{12}H_{14}F_3NO_2 = 261.25$.

|  | C | H | N % |
| --- | --- | --- | --- |
| Calculated | 55.17 | 5.40 | 5.36 |
| Found | 55.17 | 5.46 | 5.40 |

EXAMPLE 3

1-(4-butyramidophenyl) 2,2,2-trifluoroethanol

Using the same procedure as in example 1, the following compounds have been obtained:

4-butyramido ααα-trifluoroacetophenone 1-(4-butyramidophenyl) 2,2,2-trifluoroethanol melting at 120° (methanol).

ANALYSIS: $C_{12}H_{14}F_3NO_2 = 261.25$.

|  | C | H | N % |
| --- | --- | --- | --- |
| Calculated | 55.17 | 5.40 | 5.36 |
| Found | 55.52 | 5.41 | 5.37 |

EXAMPLE 4

1-(4-propionamidophenyl) 2,2,2-trifluoroethanol

Using the same procedure as in example 1, the following compounds have been obtained:

4-propionamido ααα-trifluoroacetophenone 1-(4-propionamidophenyl) 2,2,2-trifluoroethanol as colourless crystals melting at 166°–167° (water).

ANALYSIS: $C_{11}H_{12}F_3NO_2 = 247.22$.

|  | C | H | N % |
| --- | --- | --- | --- |
| Calculated | 53.44 | 4.89 | 5.67 |
| Found | 53.35 | 4.89 | 5.67 |

EXAMPLE 5

1-[(4-chlorobenzoylamino)phenyl] 2,2,2-trifluoroethanol

Using the same procedure as in example 1, the following compounds have been obtained:

4-(chlorobenzoylamino) ααα-trifluoroacetophenone
1-[(4-chlorobenzoylamino)phenyl] 2,2,2-trifluoroethanol melting at 175°-176° (water).
ANALYSIS: $C_{15}H_{11}ClF_3NO_2 = 329.71$.

|  | C | H | N % | Cl % |
|---|---|---|---|---|
| Calculated | 54.63 | 3.36 | 4.25 | 10.75 |
| Found | 54.39 | 3.54 | 4.49 | 11.14 |

EXAMPLE 6

1-[(4-nicotinoylamino)phenyl] 2,2,2-trifluoroethanol

Using the same procedure as in example 1 and starting from 18.9 g of 4-amino ααα-trifluoroacetophenone and 17.8 g nicotinoylchloride, 13.5 g of 4-(nicotinoylamino) ααα-trifluoroacetophenone are obtained.

Using the reduction method with sodium borohydride according to example 1 step C, 1-[(4-nicotinoylamino)phenyl] 2,2,2-trifluoroethanol is obtained with a yield of 88%. The pure compound melts at 214°-215° (water).
ANALYSIS: $C_{14}H_{11}F_3N_2O_2 = 300.75$.

|  | C | H | N % |
|---|---|---|---|
| Calculated | 55.91 | 3.82 | 9.31 |
| Found | 55.97 | 3.79 | 9.36 |

EXAMPLE 7

1-[(4-methylpiperazinyl)-4 phenyl] 2,2,2-trifluoroethanol

Using the procedure of example 1, the following compounds have been obtained:

4-(4-methylpiperazinyl-1) ααα-trifluoroacetophenone melting at 54°-55°

1-[4-(4-methylpiperazinyl-1)phenyl] 2,2,2-trifluoroethanol melting at 192°.
ANALYSIS: $C_{13}H_{17}F_3N_2O = 274.29$.

|  | C | H | N % |
|---|---|---|---|
| Calculated | 56.93 | 6.25 | 10.21 |
| Found | 57.04 | 6.36 | 10.20 |

EXAMPLE 8

1-(4-n hexadecylaminophenyl) 2,2,2-trifluoroethanol

Step A 4-n-hexadecylamino 2,2,2-trifluoroacetophenone

In a three-neck flask 30 g 4-fluoroααα-trifluoroacetophenone, 44.5 g freshly redistilled n-hexadecylamine, then 21.55 g sodium carbonate and 75 ml anhydrous dimethylsulfoxide are added. The whole mixture is heated to 100° under stirring and the heating is continued for 6 to 7 hours. After allowing the suspension to revert to room temperature, it is poured into 400 ml water. The mixture is then stirred for one hour and extracted 3 times with 30 ml ether. The aqueous phase is discarded and the ethereous phases are united, washed with water, dried over magnesium sulphate, and then evaporated off.

58.5 g of an oily product are thus obtained which essentially consists of 4-(n hexadecylamino) 2,2,2-trifluoroacetophenone.

This compound is used as such for the next step of the synthesis.

Step B 4-(n-hexadecylaminophenyl) 2,2,2-trifluoroethanol 54 g of 4-(n-hexadecylamino) 2,2,2-trifluoroacetophenone obtained from step A are dissolved in 260 ml methanol. To the solution 9.97 g sodium borohydride are added while keeping the mixture temperature below 10° using an external cooling.

The mixture is kept under stirring for 4 hours then the excess of reagent is destroyed by adding enough acetic acid. The mixture is diluted by adding an equal volume of water, then after a period of one hour of stirring, the appeared precipitate is separated and washed with water until the washings are neutral. The precipitate is dried in an oven at 60° under reduced pressure. 50.7 g (4-n-hexadecylaminophenyl) 2,2,2-trifluoroethanol are recovered and further purified by recrystalization from isopropyl ether. The pure compound melts at 63°-64°.
ANALYSIS: $C_{24}H_{40}F_3NO = 415.59$.

|  | C | H | N % |
|---|---|---|---|
| Calculated | 69.36 | 9.70 | 3.37 |
| Found | 69.40 | 9.39 | 3.45 |

This product is soluble in dilute solutions of acids such as hydrochloric acid or acetic acid. The thus-formed addition salt may be obtained by evaporating off the solvent.

EXAMPLE 9

4]4-(2,2,2-trifluoro 1-hydroxyethyl) phenylamino] 1-(2-phenylethyl)piperidine

Using the same procedure as in example 1 or in example 8 and starting from 1-(2-phenylethyl)-4-aminopiperidine, there are successively produced:

4-[4-(2,2,2-trifluoro 1-oxoethane) phenylamino] 1-(2-phenylethyl) piperidine

4-[4-(2,2,2-trifluoro 1-hydroxyethyl) phenylamino] 1-(2-phenylethyl) piperidine which latter melts at 120°-122° (ether-pentane).

This compound is soluble in the just calculated amount of N/10 hydrochloric acid. By evaporation of the solvent the corresponding hydrochloride is obtained.
ANALYSIS: $C_{21}H_{25}F_3N_2O = 378.44$.

|  | C | H | N % |
|---|---|---|---|
| Calculated | 66.63 | 6.66 | 7.40 |
| Found | 66.68 | 6.85 | 7.27 |

EXAMPLE 10

1-(4-acetamidophenyl) 1-ethoxy 2,2,2-trifluoroethane 6.6 g of 4-p.acetamidophenyl 2,2,2-trifluoroethanol from example 1 are dissolved in 75 ml ethanol at room temperature. To this solution a solution previously prepared in reacting 0.5 g freshly cut sodium with 25 ml ethanol is cautiously added. The whole mixture is kept under stirring for one hour and evaporated to dryness under reduced pressure. The resulting sodium derivative is taken up in 30 ml dimethylformamide at room temperature. After complete dissolution, the solution is cooled to 10° and to this solution, 4.2 ml ethyl bromide previously cooled to 0° are added, while avoiding an increase of the inner temperature by immersing the flask in an iced water bath. The temperature is then allowed to revert to room temperature, and the stirring is maintained for 4 hours.

The mixture is thereafter diluted with water and extracted several times with methylene chloride. The organic phases are separated, washed with a 5% sodium carbonate solution then with water, dried and evaporated off.

The oily residual product gradually crystallizes. 6.35 g of raw product are thus recovered by filtration. They are taken up in a few ml of benzene and the solution is diluted with cyclohexane. After one hour standing in a cool place, 1-(4-acetamidophenyl) 1-ethoxy 2,2,2-trifluoroethane precipitates. It is further purified by chromatography on silica and elution with a 50:50 mixture of cyclohexane and ethylacetate. 2.9 g of pure compound are obtained from the eluates. It melts at 132°–134°.

ANALYSIS: $C_{12}H_{14}F_3NO_2 = 261.25$.

|  | C | H | N % |
|---|---|---|---|
| Calculated | 55.17 | 5.40 | 5.36 |
| Found | 55.33 | 5.48 | 5.43 |

This compound is insoluble in water but soluble in most of the organic solvents.

EXAMPLE 11 dl 1-[(4-cyclobutylamino) phenyl] 2,2,2-trifluoroethanol

Using the same procedure as in example 1 and in example 8 and starting from dl cyclobutylamine, dl[(4-cyclobutylamino) phenyl] 2,2,2-trifluoroethanol is obtained melting at 90°–92°.

ANALYSIS: $C_{12}H_{14}F_3NO = 245.75$.

|  | C | H | N % |
|---|---|---|---|
| Calculated | 57.71 | 5.82 | 5.62 |
| Found | 57.60 | 5.79 | 5.31 |

EXAMPLE 12 dl 1-[(4-cyclopentylamino) phenyl] 2,2,2-trifluoroethanol

Using the same procedure as in example 1 and in example 8 and starting from cyclopentylamine, 1-[(4-cyclopentylamino) phenyl] 2,2,2-trifluoroethanol is obtained which melts at 100°–101°.

ANALYSIS: $C_{13}H_{16}F_3NO = 259.27$.

|  | C | H | N % |
|---|---|---|---|
| Calculated | 60.22 | 6.22 | 5.40 |
| Found | 59.96 | 6.47 | 5.40 |

EXAMPLE 13 dl 1-(4-tertbutylaminophenyl) 2,2,2-trifluoroethanol

Using the procedure of example 8 and starting from tertbutylamine, the following are successively obtained:

1-(4-tertbutylamino) 2,2,2-trifluoroacetophenone Eb = 120/0.05 mm Hg, 1-(4-tertbutylaminophenyl) 2,2,2-trifluoroethanol MP 87°–89°.

ANALYSIS: $C_{12}H_{16}F_3ON = 247.26$.

|  | C | H | N | F % |
|---|---|---|---|---|
| Calculated | 58.53 | 6.14 | 5.69 | 23.14 |
| Found | 58.39 | 6.21 | 5.74 | 23.09 |

IR Spectrum: lack of carbonyl stretchings

EXAMPLE 14

Tablets containing each 300 mg 1-(4-acetamidophenyl) 2,2,2-trifluoroethanol

| 1-(4-acetamidophenyl)2,2,2-trifluoroethanol | 3kg |
|---|---|
| wheat starch | .950kg |
| lactose | .250kg |
| sodium alginate | .100kg |
| formulated casein | .100kg |
| polyvinylpyrolidone | .065kg |
| titanium silicate | .065kg |
| magnesium silicate | .100kg |
| talc | .285kg | for 10,000 tablets weighing each 0.500 g

EXAMPLE 15

Suppositories containing 250 mg of 4-(n-hexadecylaminophenyl) 2,2,2-trifluoroethanol

| 4-(n-hexadecylaminophenyl)2,2,2-trifluoroethanol | 5kg |
|---|---|
| yellow-orange lack S | .006kg |
| colloidal silica | .280kg |
| polyethylene glycol stearates | 26kg114 | for 20,000 suppositories having an average weight of 1.4 g.

EXAMPLE 16

Pharmacological study of the compounds of formula I:
(a) acute toxicity:

The acute toxicity of the compounds of formula I has been determined on batches of mice from swiss strain which receive by oral administration the compounds to be tested at increasing dosages. The mice are kept under survey for 8 days and the deaths, if any, are counted.

The experimented doses range from 800 mg/kg to 4,000 mg/kg. For most of the compounds, mortality in mice appears only at doses as high as 1.5 g/kg. The average lethal doses graphically determined are usually close to 2 g/kg.

(b) determination of the anti-inflammatory effect:

The anti-inflammatory action of the compound of formula I has been determined according to the method disclosed by Winter by the carrageenin test in rats.

Batches of 10 rats from WISTAR strain, previously fasted for 12 hours, receive subcutaneously the compounds to be tested in an aqueous suspension or solution.

One half-hour after, the plantar aponevrosis of the right paw is injected with a 1% solution of carrageenin. The volume of the injected paw of the rats is measured 3 hours after this injection in comparison with that of the untreated paw. The doses of the tested compounds range from 20 to 320 mg/kg. Generally speaking the average dose which reduce from 50% the volume of the inflammated paw in comparison of the volume of the normal paw is about 150 mg/kg.

(c) determination of the analgesic effect:

The analgesic effect of the compounds of formula I has been determined using the WRITHING test after intraperitoneal injection of phenylbenzoquinone according to the method disclosed by HENDERSHOT (J. Expt. Pharm. Therap. 125 (1959) 237).

Batches of 10 mice (swiss strain) receive intraperitoneally an injection of 1 mg/kg phenylbenzoquinone. Prior to this injection, the mice receive orally either in solution or in suspension in aqueous vehicle, the compounds to be tested at doses ranging between 25 and 400 mg/kg. The average active doses which decrease by 50% the number of writhings in the mice in comparison with the controls which receive only phenylbenzoquinone vary, depending on the compound, from 50 to 100 mg/kg.

(d) determination of the antipyretic effect:

The antipyretic effect of the compounds of formula I has been determined according to the method described by J. J. LOUX and cowork. Toxicol. and Appl. Pharmacol. 22 (1972) 672. According to this method a hyperthermic crisis occurs in the rats after subcutaneous injection of baker yeast.

The compounds to be tested are administered orally in a suspension of an arabic gum solution 19 hours after the injection of yeast.

The body temperatures are measured from 1 to 5 hours after the ingestion of the compounds of formula I by means of a thermistor. The dosages tested range from 25 to 200 mg/kg.

The increase of body temperature in the control rats is about 2° in comparison of that of the untreated rats. The animals which receive the compounds of formula I show only a moderate increase of temperature, mainly 3 and 4 hours after the ingestion of the tested compound. The highest dosages (150 and 200 mg/kg) caused a return to the initial temperature in the treated animals.

In similar experimental conditions, batches of rats receive paracetamol at dose ranging from 50 to 500 mg. The useful dose which curbs signicantly the increase of temperature is about twice of that of the compounds of formula I.

What we claim is:

1. The ααα-trifluoro (aminoaryl) ethanols having the formula I:

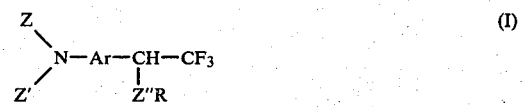

wherein
Z is an N-lower alkylpiperidine radical or an N-(phenyl lower alkyl)piperidine radical,
Z' is a hydrogen or a lower alkyl radical,
Z" is an oxygen atom,
Ar is phenyl, and
R is hydrogen.

2. An acid addition salt of a compound of claim 1 with a mineral or organic acid.

3. The optically-active isomers of a compound of claim 1 or 2.

4. A compound of claim 1, which is dl 4-[4-(2,2,2-trifluoro 1-hydroxyethyl) phenylamino] 1-(2-phenylethyl) piperidine.

5. A pharmaceutical composition useful for the treatment of inflammation incorporating as active ingredient an anti-inflammatory pain-alleviating effective amount of a compound of claim 1.

6. A pharmaceutical composition according to claim 5, wherein the amount of active ingredient ranges from 50 to 600 mg per unit dosage.

7. A pharmaceutical composition according to claim 5, wherein the active ingredient is dl 4-[4-(2,2,2-trifluoro 1-hydroxyethyl) phenylamino] 1-(2-phenylethyl)piperidine.

8. A pharmaceutical composition according to claim 6, wherein the active ingredient is dl 4-[4-(2,2,2-trifluoro 1-hydroxyethyl) phenylamino] 1-(2-phenylethyl)piperidine.

9. A method for the alleviation of pain and inflammation in a patient suffering therefrom, comprising the step of administering to said patient an effective anti-inflammatory pain-alleviating effective amount of a compound of claim 1.

10. The method of claim 9, wherein the effective amount is in the range of 0.1 g to 3 g daily.